United States Patent [19]

Hertl et al.

[11] 4,166,006

[45] Aug. 28, 1979

[54] MEANS FOR STIMULATING MICROBIAL GROWTH

[75] Inventors: William Hertl; William S. Ramsey, both of Corning, N.Y.

[73] Assignee: Corning Glass Works, Corning, N.Y.

[21] Appl. No.: 850,222

[22] Filed: Nov. 10, 1977

[51] Int. Cl.² ............................................. C12B 1/20
[52] U.S. Cl. ................................................... 435/244
[58] Field of Search ................................ 195/109, 114

[56] References Cited

U.S. PATENT DOCUMENTS 3,041,250   6/1962   Wolnak et al. ........................ 195/109
3,850,753   11/1974   Chibata et al. ........................ 195/109

*Primary Examiner*—Alvin E. Tanenholtz
*Attorney, Agent, or Firm*—William E. Maycock; Clinton S. Janes, Jr.; Clarence R. Patty, Jr.

[57] ABSTRACT

This invention is concerned with the use of fluorocarbon and silicone oil greases or gels to stimulate the growth of various microorganisms. More particularly, the instant invention contemplates the addition of a peroxide compound, preferably hydrogen peroxide ($H_2O_2$), to fluorocarbon and silicone oil greases or gels to further stimulate the growth of anaerobes and facultative anaerobes in liquid or solid nutrient media.

5 Claims, No Drawings

MEANS FOR STIMULATING MICROBIAL GROWTH

BACKGROUND OF THE INVENTION

Bacteria may be categorized into three fundamental groups based upon their growth relationship to oxygen: first, there are the aerobes which require oxygen for growth; second, there are the anaerobes which do not require the presence of oxygen for growth; and, third, there are the facultative anaerobes which have the capability for growing both in the presence of or in the absence of oxygen. With regard to the third group, however, facultative anaerobes derive more energy from nutrient materials aerobically than anaerobically and, consequently, develop more rapidly and to higher concentrations in the presence of oxygen rather than anaerobically.

One common method for obtaining large numbers of microorganisms for industrial use or for identification in clinical laboratories is to inoculate a specimen of the microorganisms into a liquid nutrient medium. If the microorganism is an aerobe, the oxygen level within the medium will become depleted within a relatively short period of time, thereby reducing further growth of the microorganism within the medium. Replenishment of the oxygen content in a liquid medium has customarily been accomplished in two ways: (1) by shaking the medium to provide a large surface area for gaseous exchange with the ambient air; or (2) by bubbling air or oxygen through the medium. Both methods have economic and practical shortcomings. Shaking demands space for large and expensive shaking equipment. Bubbling requires a source of compressed air or oxygen and hazards contamination of the culture by organisms entrained within the gas. As a natural consequence, then, many cultures are merely incubated in tubes with oxygen replenishment being dependent solely upon diffusion from the ambient air (Lennette, I. H., Spaulding, E. H., and Truant, J. P., *Manual of Clinical Microbiology*, 2nd Ed., American Society for Microbiology, 1974). It is obvious that the growth rates and total growth contents of such cultures will be severely limited when compared with fully aerated cultures. Yet, the time required for microbial growth constitutes a substantial proportion of the time employed in clinical microbiology services. It is believed evident that such services would be considerably improved if the time demanded for culture growth could be reduced significantly.

It is well known that oxygen is very soluble in certain silicone oils and fluorocarbon liquids. Thus, the solubility of oxygen in those liquids is many times greater than that in water. That characteristic of those materials has led to laboratory experiments wherein cats and mice have survived being immersed into such oxygen-saturated fluids for as long as several hours; air or oxygen being bubbled through the fluid (Golan, Frank, "Survival of Mammals Breathing Organic Fluids Equilibrated with Oxygen at Atmospheric Pressure," *Science*, 152, pp. 1755–6, June 24, 1966). As an extension of that work, those liquids have been brought into contact with solid and liquid nutrient media to accelerate the growth of microorganisms therein. That practice has indeed enhanced both the rate of growth and the level of growth of oxygen-utilizing microorganisms.

However, to insure air or oxygen-saturation of those fluids has required the above-mentioned shaking or bubbling techniques, both of which are cumbersome and economically unattractive. Therefore, the primary objective of this invention is to devise means for providing even larger amounts of air or oxygen than are soluble into those liquids, thereby making it possible to achieve even greater enhancement of aerobic and facultative anaerobic microorganism growth than that obtained via the use of the liquids alone. Also, this inventive means would not require shaking or bubbling to be effective.

SUMMARY OF THE INVENTION

We have found that object can be achieved where a peroxide compound is admixed with fluorocarbon or silicone oil greases or gels and the resultant mixture brought into contact with a solid or liquid nutrient medium.

The ability of many peroxides to release oxygen is a well-recognized chemical phenomenon, the rate of oxygen generation being a function of the temperature involved and the specific peroxide employed. Peroxides, however, are also well known to those skilled in the art as being highly toxic to bacteria. Indeed, hydrogen peroxide is widely regarded as a germicide and is in very common use as a disinfectant. Peroxides perform very effectively as germicides because their decomposition takes place via a free radical mechanism which produces highly reactive, and therefore toxic, oxygen atoms. After a brief period of time, those oxygen atoms can recombine, unless they have reacted with other elements. Furthermore, any organic compounds readily react with hydrogen peroxide, some explosively.

Liquid fluorocarbons and silicone oils, such as dimethyl silicone oil and phenylmethyl silicone oil, are essentially water-immiscible, non-nutritive, non-toxic, and inert to the microorganisms. In the exemplary embodiments of the invention reported hereinafter, Fluoroinert Brand Electronic Liquid, FC-75, marketed by Minnesota Mining and Manufacturing Company, comprised the liquid fluorocarbon, and dimethyl silicone oil 1000 cs, marketed by Dow Corning Company, was employed as the silicone oil.

The use of fluid fluorocarbons provides a slightly greater enhancement of bacterial growth than does silicone oil due to the higher oxygen solubility. Nevertheless, that advantage is believed to be outweighed by the following two practical factors:

(1) silicone oil is substantially non-volatile at temperatures required for sterilization and, thus, can be conveniently sterilized by autoclaving or by simply heating to 121° C., whereas, because the fluorocarbons are somewhat volatile at such temperatures, they must be sterilized by filtering to remove bacteria, if losses of the fluids are to be minimized; and (2) liquid fluorocarbons are several times more expensive than silicone oils.

When cultures of microorganisms such as bacteria are grown in solid media in petri dishes, it is customary to invert the petri dish during incubation to preclude condensed water droplets from falling back onto the surface of the medium. Where water droplets are permitted to contact the medium, the cultures become smeared and mixed together, thereby becoming useless. The liquid fluorocarbons and some silicone oils have a higher density than the conventional nutrient media. Nevertheless, when a liquid fluorocarbon or silicone oil is placed in the bottom of a petri dish and the nutrient medium floated thereupon, it is not possible to safely invert the dish since the medium will slump and the underlying liquid will be released. Accordingly, inert fillers in fine particulate form, e.g., powdered silica, can be added to the liquids to "immobilize" them and yield greases or gels. This practice renders it possible to simultaneously obtain the advantages of an oxygen source at the bottom of the medium, while also allowing the petri dishes to be inverted to forestall spoiling the cultures with droplets of condensed water. In addition, the thickening of the liquids to greases supplies a firm base which enables the medium to resist distortion during streaking or other manipulations.

It is of interest to observe that water in fairly substantial amounts can be incorporated into the greases via stirring. The grease itself, however, retains its "hydrophobic" character with respect to contact with aqueous solutions.

$H_2O_2$ is the preferred peroxide for the inventive method because it decomposes at the incubation temperatures of the microorganisms, it is convenient to use, and it is relatively inexpensive.

DESCRIPTION OF PREFERRED EMBODIMENTS

To illustrate the effectiveness in enhancing the growth of microorganisms demonstrated by the presence of liquid fluorocarbons and silicone oils, the following work was conducted, the results of which are reported in Table I.

A sample of nutrient broth marketed by Difco Laboratories was inoculated with *Escherichia coli*. Samples of the Fluoroinert Brand Electronic Liquid and Dimethyl Silicone oil 1000 cs were saturated by bubbling air or oxygen therethrough for 10–60 minutes. Five ml specimens of those liquids were incubated with five ml of inoculated nutrient broth in unsealed tubes at 37° C. for the periods of time recited in Table I. A comparison of the optical densities is recorded with a control sample consisting solely of inoculated nutrient broth. The optical density of uninoculated broth has been subtracted from each reading.

TABLE I

| Duration of Incubation (minutes) | Control Sample | Silicone Oil Air Saturated | Silicone Oil Oxygen Saturated | Fluorocarbon Air Saturated | Fluorocarbon Oxygen Saturated |
|---|---|---|---|---|---|
| 0 | 0.035 | 0.035 | 0.035 | 0.035 | 0.035 |
| 60 | 0.087 | 0.093 | 0.108 | 0.091 | 0.108 |
| 120 | 0.107 | 0.112 | 0.117 | 0.117 | 0.115 |
| 180 | 0.111 | 0.122 | 0.126 | 0.121 | 0.134 |
| 240 | 0.107 | 0.126 | 0.148 | 0.137 | 0.157 |

A review of the results immediately confirms the enhancement of microbial growth imparted by the fluorocarbon and silicone oils.

In order to immobilize the oils, the following two greases were formulated:

| Flourocarbon oil | 94.4g | Silicone oil | 200 ml |
|---|---|---|---|
| Powdered silica | 10.7 | Powdered silica | 50g |
| DC-190 stabilizer | 0.2 ml | DC-190 stabilizer | 0.2 ml |

(DC-190 stabilizer is a silicone-polyoxyalkylene copolymer marketed by Dow Corning)

As can readily be appreciated, the viscosities of the greases can be modified by varying the silica loading or quantity of stabilizer. One very practical discovery was made with both of the above-cited formulations; viz., each was found to be stable after autoclaving in a steam atmosphere at 121° C. This factor eliminated the need to filter the fluorocarbon oil to remove bacteria therefrom.

In like manner to the cultures described above in Table I, a sample of nutrient broth was inoculated with *Escherichia coli*. About five grams of the fluorocarbon or silicone oil grease, which had been saturated with air or oxygen by diffusion, were placed in the bottom of a tube and five ml of the inoculated liquid nutrient broth poured thereupon. The mixtures were incubated in unsealed tubes at 37° C. for the periods of time reported in Table II. A comparison of the optical densities is provided with a control sample comprising the inoculated nutrient broth alone. The optical density of the uninoculated nutrient medium has been deducted from each result reported.

Table II

| Duration Incubation (minutes) | Control Sample | Silicone Oil Grease Air Saturated | Silicone Oil Grease Oxygen Saturated | Flourocarbon Grease Air Saturated | Flourocarbon Grease Oxygen Saturated |
|---|---|---|---|---|---|
| 0 | 0.038 | 0.038 | 0.047 | 0.038 | 0.047 |
| 30 | 0.049 | 0.051 | 0.063 | 0.064 | 0.065 |
| 60 | 0.051 | 0.061 | 0.086 | 0.075 | 0.074 |
| 120 | 0.068 | 0.076 | 0.135 | 0.084 | 0.103 |
| 180 | 0.076 | 0.091 | 0.181 | 0.104 | 0.131 |
| 240 | 0.082 | 0.099 | 0.198 | 0.117 | 0.135 |
| 300 | 0.085 | 0.114 | 0.235 | 0.113 | 0.151 |

A study of these data clearly manifests the increased bacterial growth resulting from the presence of the greases.

When samples of melted solid nutrient media, which had been inoculated with *E. coli*, were poured into tubes containing either of the above-described greases saturated with air or oxygen and thereafter allowed to cool and incubate, growth of the microorganisms was observed at the top or air interface down to a depth of about 1 mm. Such, of course, represents customary behavior. However, about an equal amount of growth was observed at the bottom of the medium in each tube at the interface with the grease, thereby unequivocally demonstrating the faculty of the grease to act as a source of oxygen.

The following procedure illustrates the fact that the oxygen supplying capability of the above-described oxygenated greases can be utilized to provide the transport of oxygen through solid nutrient agar and thereby affect the growth of bacterial colonies on the surface of the agar. Approximately 19 grams of each grease were individually spread over the bottom of separate 100 mm diameter petri plates and the plates were then exposed to oxygen gas for one hour. Subsequently, 20 ml of nutrient agar at 48° C. were poured onto each plate and permitted to solidify and cool. The plates were thereafter inoculated on the surface of the agar with a suspension of *Escherichia coli*, inverted and then incubated overnight at 37° C. Typical plates were taken and all of the individual colonies of bacteria were measured (at least 60 for each plate) with the results observed being recorded below:

|  | Average Colony Area (mm$^2$) |
| --- | --- |
| Control plate (no grease) | 6.03 |
| Silicone grease | 9.95 |
| Flourocarbon grease | 9.76 |

It is quite apparent that colonies of *E. coli* from both the silicone and fluorocarbon plates were significantly larger than the control colonies.

In summary, the above procedure clearly illustrates two very practical advantageous of utilizing oxygenated grease:

(1) with this unique configuration of solid medium and grease, one can obtain about double the number of bacteria in a given period of time when compared to a conventional configuration; and (2) simultaneously with the substantially improved microbial growth, one can invert petri dishes during the incubation period so as to thereby enjoy the best recommended techniques for incubation.

Table III records the findings of procedures conducted to illustrate the even greater enhancement in microbial growth which can be achieved through the addition of hydrogen peroxide to the fluorocarbon or silicone oil greases. The mechanism underlying the invention is based upon providing even larger amounts of oxygen than are soluble in those materials.

A grease was formulated consisting of the above-described silicone oil, powdered silica, and $H_2O_2$ in the following proportions:

| Silicone oil | 100 g |
| --- | --- |
| Powdered silica | 16 g |
| 30% aqueous $H_2O_2$ | 3% by volume |

About 5 ml of this $H_2O_2$-containing grease was deposited into each of ten tubes. About 1 ml of the same grease, but without $H_2O_2$, was placed on top of the grease samples in the tubes. Control samples containing only silicone grease and no added grease were also prepared. Ten ml of the above-described nutrient medium containing *E. coli* bacteria were added to each of the tubes and the resultant composite incubated at 37° C. Optical density measurements were undertaken at the reported times to follow the bacterial growth rate. Again, the optical density of the uninoculated nutrient medium has been substracted from each measurement recorded.

TABLE III

| Duration Incubation (minutes) | Control Sample | Oxygenated Grease + Nutrient | Grease + $H_2O_2$ + Nutrient |
| --- | --- | --- | --- |
| 0 | 0.049 | 0.050 | 0.054 |
| 30 | 0.059 | 0.056 | 0.068 |
| 60 | 0.068 | 0.070 | 0.080 |
| 120 | 0.086 | 0.091 | 0.105 |
| 180 | 0.090 | 0.109 | 0.120 |
| 240 | 0.095 | 0.110 | 0.152 |
| 300 | 0.100 | 0.130 | 0.178 |
| 360 | 0.110 | 0.141 | 0.229 |
| 420 | 0.118 | 0.150 | 0.250 |

Table III clearly dramatizes the beneficial effect which the inclusion of $H_2O_2$ in the silicone oil grease has upon the growth of the *E. coli*. Thus, whereas the presence of the oxygenated grease aids in the growth of the microorganisms, it is evident that the presence of $H_2O_2$ greatly enhances their development. Such a result is of extreme significance since no ancillary equipment is necessary to preliminarily oxygenate the grease. Hence, the use of $H_2O_2$ is very attractive economically.

Table IV records another set of cultures wherein *Staphylococcus aureus* comprised the microorganism. Three ml of distilled water were added to 100 grams of the above-described grease composition, but without the $H_2O_2$, and five ml of the resulting mixture placed in the bottom of ten tubes. Five ml of the above-described grease composition (containing $H_2O_2$) were deposited in the bottom of ten other tubes. Finally, ten empty tubes were gathered. Ten ml of an overnight culture of *S. aureus* were added to 200 ml of nutrient broth. Five ml of the resultant suspension were added to each of the referred-to 30 tubes and the mixtures incubated at 37° C. Optical density measurements were made at the reported times to monitor the bacterial growth. (The optical density of the uninoculated nutrient medium has been subtracted from each of the reported determinations.)

TABLE IV

| Duration of Incubation (minutes) | Control Sample | Water + Grease | $H_2O_2$ + Grease |
| --- | --- | --- | --- |
| 0 | 0.05 | 0.05 | 0.056 |
| 30 | 0.056 | 0.056 | 0.063 |
| 60 | 0.065 | 0.067 | 0.072 |
| 120 | 0.065 | 0.084 | 0.098 |
| 180 | 0.068 | 0.100 | — |
| 240 | 0.076 | 0.110 | 0.220 |

Table IV is believed to illustrate two substantive facts. First, the use of $H_2O$ does not provide the same increase in bacterial growth imparted by $H_2O_2$. Second, the inclusion of $H_2O_2$ in the silicone oil grease greatly enhances growth of the microorganisms.

Table V demonstrates the stability of the $H_2O_2$-containing mixtures. Thus, greases were compounded consisting of 100 parts of silicone oil plus 3% by volume of 30% $H_2O_2$ aqueous solution to which varying proportions of powdered silica (4, 8, 12, and 16 parts by weight) were added. The resulting greases were either stored in a refrigerator at 9° C. or in a freezer at −7° C. After storage for varying lengths of time, the greases were removed, incubated at 37° C. for stated periods of time, and the amount of oxygen gas evolved during the incubation measured.

TABLE V

| Days Stored and Storage Temperature | Incubation at 37° C. | Oxygen Evolved with 4 Parts Silica Sample | Oxygen Evolved with 8 Parts Silica Sample | Oxygen Evolved with 12 Parts Silica Sample | Oxygen Evolved with 16 Parts Silica Sample |
|---|---|---|---|---|---|
| 0 | 5 hrs. | 3.8 ml | 5.4 ml | 6.6 ml | 6.8 ml |
| 0 | 7 hrs. | 4.8 ml | 6.4 ml | 8.8 ml | 7.8 ml |
| 7 at 9° C. | 5 hrs. | — | — | — | 4.6 ml |
| 7 at −7° C. | 5 hrs. | — | — | — | 8.2 ml |
| 14 at 9° C. | 5 hrs. | — | — | — | 4.4 ml |
| 14 at −7° C. | 5 hrs. | — | — | — | 6.6 ml |
| 21 at −7° C. | 5 hrs. | — | — | 7.0 ml | 6.8 ml |
| 28 at −7° C. | 6 hrs. | — | — | 6.8 ml | 7.0 ml |
| 34 at −7° C. | 8 hrs. | — | — | 7.0 ml | — |
| 34 at 9° C. | 8 hrs. | — | — | — | 2.0 ml |
| 42 at −7° C. | 7.5 hrs. | — | 7.8 ml | 7.6 ml | — |
| 56 at −7° C. | 7.5 hrs. | 6.0 ml | 8.0 ml | — | — |
| 63 at −7° C. | 8 hrs. | 6.4 ml | 8.6 ml | — | — |
| 70 at −7° C. | 8 hrs. | 5.0 ml | — | — | — |
| 70 at 9° C. | 8 hrs. | — | — | 3.0 ml | — |

From the foregoing specific working examples, it is believed evident that the instant invention is useful for enhancing the growth of any microorganism which utilizes the presence of oxygen, i.e., aerobes and facultative anaerobes. Most of the bacteria of clinical interest, e.g., *Escherichia coli* and *Staphylococcus aureus*, are facultative anaerobes.

As was explained above, $H_2O_2$ comprises the preferred peroxide for the invention because it readily decomposes, releasing oxygen, at temperatures utilized in the incubation of microorganisms, viz., greater than 0° C. but less than about 75° C. Nevertheless, it will be recognized that any peroxide compound capable of decomposing within that temperature range which does not release toxic gases into the nutrient medium and which does not react with the fluorocarbon or silicone oil would also be operable, e.g., benzoyl peroxide and lauroyl peroxide. Furthermore, whereas a commercially-marketed 30% by weight aqueous solution of $H_2O_2$ was employed in the above examples, such as a matter of convenience only. Greater or lower concentrations of $H_2O_2$ can be utilized but, in general, high concentrations are deemed more desirable since, obviously, larger amounts of oxygen will be expelled for the same amount of solution involved. Finally, whereas powdered silica was employed as a filler in the above exemplary compositions, and such is preferred because of the high attraction of its surface for the adsorption of materials thereto, it will be appreciated that other fillers are operable so long as such fillers provide the proper rheological properties to the grease or gel, and such permit the ready admixing of the peroxide. Operable materials would include powdered $Al_2O_3$ and glass.

Given this disclosure, it is thought that modification in the method described may become apparent to those skilled in the art. Consequently, the above specific examples must be deemed to be illustrative only, and that the scope of the instant invention is delineated in the following claims.

We claim:

1. A method for enhancing the growth of aerobic and facultative anaerobic microorganisms via one of the following processes which consists essentially of:
   contacting a grease consisting essentially of a fluorocarbon or silicone oil, an inert filler in fine particulate form, and a peroxide compound, with a liquid nutrient medium and an aerobic or facultative anaerobic microorganism, and incubating the resulting combination; or
   (b) contacting a solid nutrient medium with a grease consisting essentially of a fluorocarbon or silicone oil, an inert filler in fine particulate form, and a peroxide compound, inoculating the solid nutrient medium with an aerobic or facultative anaerobic microorganism, and incubating the resulting inoculated medium-grease combination;
said peroxide compound being one which is capable of decomposing at a temperature between about 0°–75° C., which does not release toxic gases into either nutrient medium and which is present in an amount which is otherwise not toxic to said microorganism, and which does not react with said grease; and said incubating is carried out at a temperature and for a time sufficient to give enhanced growth of the microorganism.

2. A method according to claim 1 wherein said inert filler is selected from the group consisting of powdered silica, $Al_2O_3$, and glass.

3. A method according to claim 1 wherein said silicone oil comprises a dimethyl silicone oil.

4. A method according to claim 1 wherein said peroxide compound is selected from the group consisting of $H_2O_2$, benzoyl peroxide, and lauroyl peroxide.

5. A method according to claim 4 wherein said peroxide compound consists of a 30% by weight aqueous solution of $H_2O_2$.

* * * * *

UNITED STATES PATENT AND TRADEMARK OFFICE
CERTIFICATE OF CORRECTION

PATENT NO. : 4,166,006
DATED : August 28, 1979
INVENTOR(S) : William Hertl and William S. Ramsey It is certified that error appears in the above-identified patent and that said Letters Patent are hereby corrected as shown below:

Column 4, Table II, Column 5, Line 31, change "Flouro-" to --Fluoro--.

Column 4, Table II, Column 6, line 31, change "Flouro-" to --Fluoro--.

Column 8, line 25, before "contacting" insert --(a)--.

Signed and Sealed this

Twenty-second Day of January 1980

[SEAL]

Attest:

SIDNEY A. DIAMOND

Attesting Officer

Commissioner of Patents and Trademarks